(12) United States Patent
Piferi

(10) Patent No.: US 10,184,997 B2
(45) Date of Patent: Jan. 22, 2019

(54) PROTECTIVE COVERS FOR RF COILS AND RELATED RF COILS, ASSEMBLIES AND METHODS

(71) Applicant: MRI Interventions, Inc., Memphis, TN (US)

(72) Inventor: Peter Piferi, Orange, CA (US)

(73) Assignee: MRI Interventions, Inc., Irvine, CA (US)

(*) Notice: Subject to any disclaimer, the term of this patent is extended or adjusted under 35 U.S.C. 154(b) by 458 days.

(21) Appl. No.: 14/287,613

(22) Filed: May 27, 2014

(65) Prior Publication Data

US 2015/0011870 A1    Jan. 8, 2015

Related U.S. Application Data

(60) Provisional application No. 61/841,971, filed on Jul. 2, 2013.

(51) Int. Cl.
*A61B 5/05* (2006.01)
*G01R 33/34* (2006.01)
*G01R 33/3415* (2006.01)
*A61B 50/30* (2016.01)
*A61B 50/00* (2016.01)

(52) U.S. Cl.
CPC .............. *G01R 33/34* (2013.01); *A61B 50/30* (2016.02); *A61B 2050/002* (2016.02); *A61B 2050/3015* (2016.02); *A61B 2050/314* (2016.02); *G01R 33/3415* (2013.01)

(58) Field of Classification Search
USPC ......................................................... 600/422
See application file for complete search history.

(56) References Cited

U.S. PATENT DOCUMENTS

| | | | |
|---|---|---|---|
| 4,920,318 A | 4/1990 | Misic et al. | |
| 5,246,775 A * | 9/1993 | Loscuito | C09J 7/04 428/131 |
| 5,396,905 A | 3/1995 | Newman et al. | |
| 7,282,915 B2 | 10/2007 | Giaquinto et al. | |
| 7,307,422 B2 | 12/2007 | Van Helvoort et al. | |
| 7,463,031 B2 | 12/2008 | Kato | |
| 8,099,150 B2 | 1/2012 | Piferi et al. | |
| 2007/0098953 A1* | 5/2007 | Stabelfeldt | A61F 13/58 428/100 |
| 2008/0216844 A1* | 9/2008 | Olfert | A61B 46/10 128/856 |
| 2008/0283290 A1* | 11/2008 | Niino | H05K 9/0001 174/350 |
| 2009/0088627 A1* | 4/2009 | Piferi | A61B 5/055 600/422 |

(Continued)

OTHER PUBLICATIONS

UltraCover™ 10 Mil Fire Retardant, Americover®, www.americover.com, 1 page, date unknown but believed to be prior to the priority date of the present application.

(Continued)

*Primary Examiner* — Joel F Brutus
(74) *Attorney, Agent, or Firm* — Myers Bigel, P.A.

(57) ABSTRACT

Protective covers that are particularly suitable for flexible RF coils include self-sticking, releasably peelable layers of film having one sticky/tacky inner surface and one non-sticky/non-tacky smooth (outer) surface.

18 Claims, 8 Drawing Sheets

(56) References Cited

U.S. PATENT DOCUMENTS

2009/0252951 A1* 10/2009 Ozaki .................. B32B 25/08
428/319.3
2013/0137969 A1* 5/2013 Jones .................. A61B 5/055
600/421
2014/0024925 A1 1/2014 Piferi

OTHER PUBLICATIONS

UltraCover™ 6 Mil Fire Retardant, Americover®, www.americover.com, 5 pages, date unknown but believed to be prior to the priority date of the present application, printed from the internet Jun. 25, 2013.

International Search Report and Written Opinion for corresponding PCT Application No. PCT/US2014/039064, 17 pages, dated Sep. 17, 2014.

* cited by examiner

PROTECTIVE COVERS FOR RF COILS AND RELATED RF COILS, ASSEMBLIES AND METHODS

RELATED APPLICATIONS

This application claims the benefit of and priority to U.S. Provisional Application No. 61/841,971, filed Jul. 2, 2013, the contents of which are hereby incorporated by reference as if recited in full herein.

FIELD OF THE INVENTION

The present invention relates generally to medical systems and apparatus and, more particularly, to devices for MRI-interventional systems.

BACKGROUND

During MRI-Guided surgeries, it can be desired to drill through bone, such as a skull, or otherwise provide access for and/or define a surgical path for passing medical interventional devices.

Fixation assemblies can be used to hold a target anatomical structure in a fixed position. Flexible RF imaging coils with open through spaces defining windows can be positioned between the fixation assemblies and the subject. To protect the RF coil from blood and other body fluids, clinicians use sterile plastic bags placed or draped over the RF coil(s) and the bags are typically taped in position. This can be a time consuming procedure.

SUMMARY

Embodiments of the invention are directed to self-sticking protective polymer sheets that attach to opposing external surfaces of RF flex coils (or other medical devices).

Embodiments of the invention are directed to one or more self-sticking sheets that can releasably stick to the RF coil(s) to completely cover external surfaces of the RF coil(s) and that are peelably removable. The self-sticking sheets can be configured to stick without requiring an adhesive and without leaving tacky/adhesive/or sticky residue on the RF coil(s) external surfaces upon removal (to thereby obviate the requirement for post-surgical cleaning).

The sheet or layers of one or more sheets of the protective cover can extend over open spaces or windows of the flexible RF coils and attach together.

The sheets or layers of one or more sheets of a protective cover can be punctured with a fixation pin extending from a fixation assembly to a patient or subject while remaining in position and without tearing.

The flex coils with the protective covers can be used with a head fixation assembly with a base formed entirely of MRI compatible material. The base can be configured to be secured to a gantry associated with an MRI scanner and to extend across a width of the gantry. The base can be configured to removably receive an MRI compatible head support frame for adjustably immobilizing the head of a patient during a medical procedure, and to allow the head support frame to be moved to any of a plurality of locations across the width of the gantry. The base can allow the head support frame to rotate about two orthogonal axes so as to be positioned at any of a plurality of angles relative to the gantry, and can allow the head support frame to slide along the base to any of a plurality of positions relative to the width of the gantry.

The head support frame can include a pair of head engagement arms that extend outwardly in adjacent, spaced-apart relationship. Each head engagement arm can have a free end and at least one head fixation member configured to engage a patient's head within the head support frame and restrain the patient's head from movement. In addition, the head support frame can be rotatable about two orthogonal axes so as to be positioned at any of a plurality of angles relative to the gantry.

In some embodiments, one of the head engagement arms has an arcuate carrier that is pivotably secured thereto and that supports a pair of spaced-apart head fixation members that extend through two layers of the sheet or through two cooperating sheets then are configured to engage a patient's head.

The head support frame is slidable along the base so as to be positioned at any of a plurality of locations across the width of the gantry.

In some embodiments of the present invention, a flexible RF coil encased in a self-sticking protective cover is attached to each head engagement arm of the head support assembly.

Head fixation assemblies according to embodiments of the present invention may be particularly suitable for placing neuro-modulation leads, such as Deep Brain Stimulation ("DBS") leads, implantable parasympathetic or sympathetic nerve chain leads and/or CNS stimulation leads, as well as other devices within the brain. Embodiments of the present invention may be suitable for a number of MRI-guided drug delivery procedures, MRI-guided ablation procedures, etc.

Further features, advantages and details of the present invention will be appreciated by those of ordinary skill in the art from a reading of the figures and the detailed description of the preferred embodiments that follow, such description being merely illustrative of the present invention.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION

Figure 1:
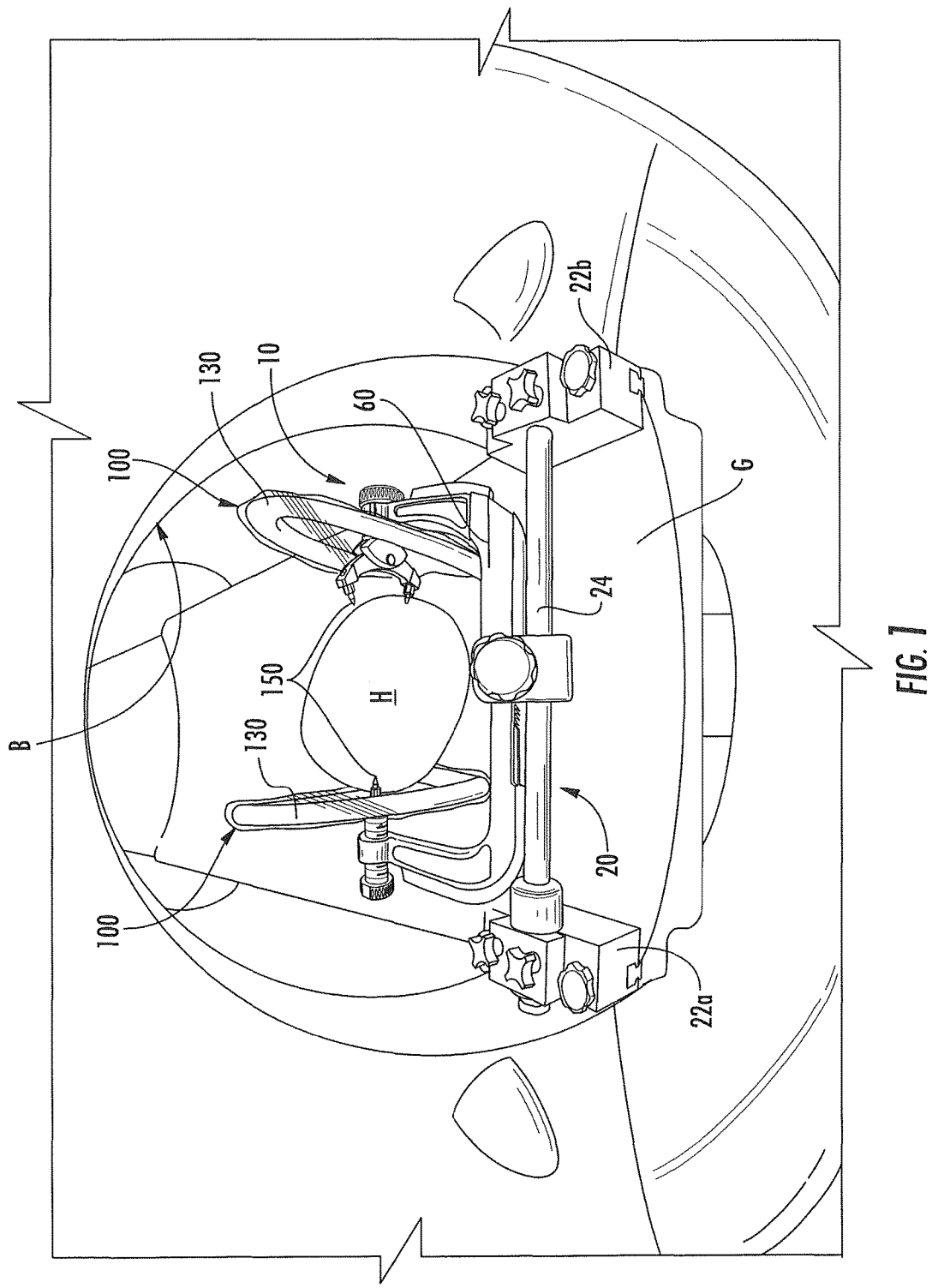
FIG. 1 is an end perspective view illustrating a pair of flexible MRI coils that can cooperate with a head fixation assembly configured to reside in a bore of an MRI magnet with a patient on a gantry, according to some embodiments of the present invention.
Figure 2A:
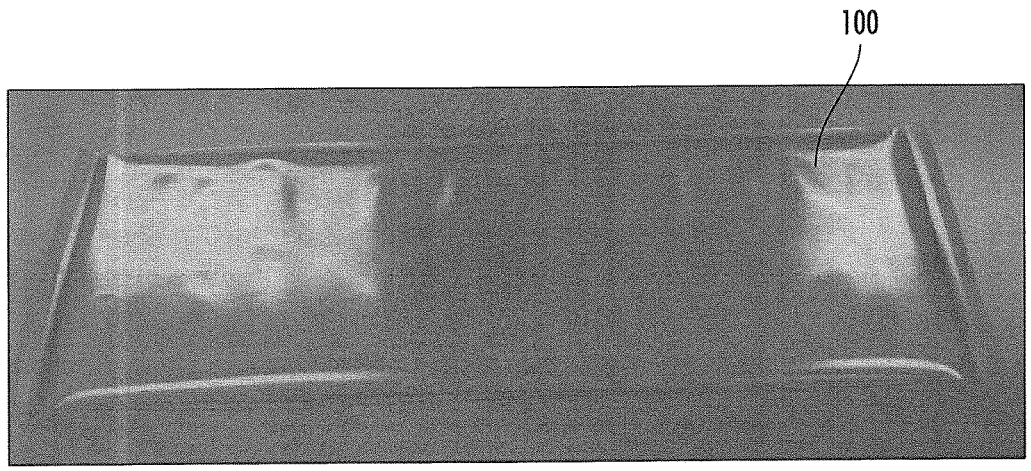
FIGS. 2A and 2B are front perspective views of an exemplary first layer of a protective cover according to some embodiments of the present invention.
Figure 2B:
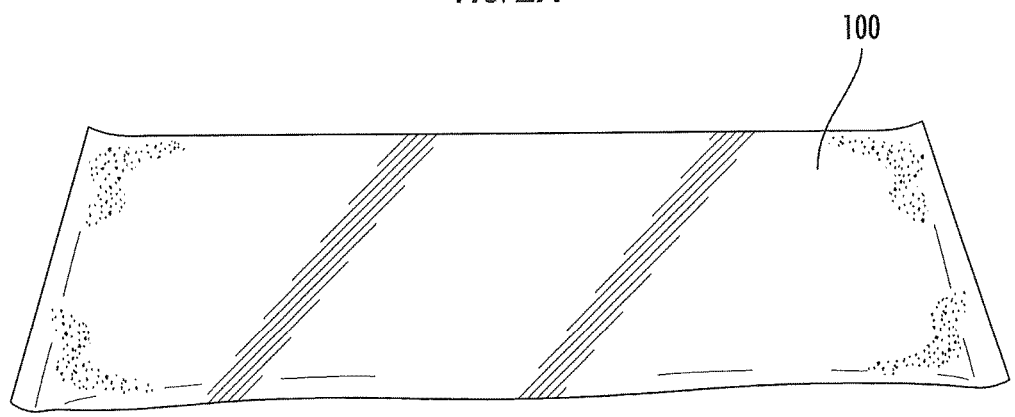

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "about", as used herein with respect to a value or number, means that the value or number can vary by +/− twenty percent (20%).

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "gantry" refers to a patient support, for example, associated with an MRI scanner, and may include a patient table or other structure.

The term "head fixation member" refers to an elongate member with sufficient structural rigidity to secure and/or move the head of a patient and may take the form of a bolt, pin, screw, etc. Head fixation members according to various embodiments of the present invention may be threaded skull pins.

The term "head fixation assembly" refers to an assembly including at least a head support frame and a base for supporting the head support frame, as described in more detail below. Head fixation assemblies according to various embodiments of the present invention can cooperate with a flex coil(s), as further described in more detail below.

The term "package" refers to any form enclosure or container of any type that holds the film irrespective of what form, e.g., the package can be configured to hold the film/covering as a roll or as a cut sheet or sheets, to protect the film during shipment/prior to use.

Head fixation assemblies according to embodiments of the present invention facilitate guiding and/or placing diagnostic or interventional devices and/or therapies to any desired internal region of the brain. For example, head fixation assemblies according to embodiments of the present invention facilitate the placement of implantable DBS leads for brain stimulation, typically deep brain stimulation, and facilitate delivering tools or therapies that stimulate a desired region of the sympathetic nerve chain. Embodiments of the present invention can be used with any MRI scanner system, including open and closed bore designs and any field strength, typically 1.0 T (Tesla)-10 T, such as about 1.5 T and 2.0 T.

Embodiments of the present invention have other uses inside or outside the brain including stem cell placement, gene therapy or drug delivery for treating physiological conditions. Some embodiments can be used to cover coils or fixation devices configured to treat tumors. Some embodiments can be used for devices for diagnosing or delivering any desired therapy such as, for example, RF stimulation or ablation, laser stimulation or ablation, cryogenic stimulation or ablation, etc.

The protective covers 100 can be conformable, flexible thin sheets of film typically sized between about 3 mils and 12 mils thick, such as about 3 mils, about 4 mils, about 5 mils, about 6 mils, about 7 mils, about 8 mils, about 9 mils or about 10 mils, for example.

The protective cover 100 can be co-extruded polyethylene film with overlying primary surfaces, one side smooth and not sticky or tacky and an opposite side that is tacky or sticky. In some embodiments, no adhesive is required to form the sticky or tacky surface. The protective cover can be an adhesive-less, self-sticking film. As flexible RF coils can be formed of delicate material(s), e.g., a thin external layer or coating over a foam-like malleable material, the new film covering is configured to attach to itself (e.g., the same sheet or a cooperating sheet of the same material) but not the RF coil and/or so as to leave no adhesive residue on the RF coils after peelably removed to thereby avoid any post-use scrubbing to remove unwanted adhesive residue left by other types of covering.

The protective cover 100 can be a pressure sensitive film that can be manually easily readably peelably removed by a clinician or clinic personnel from the coil 130 after use.

The protective cover can be visually transmissive (e.g., transparent, translucent) or can be opaque. An example of a suitable material is the ULTRACOVER™ adhesive-less film from Americover, Escondido, Calif. The protective cover may be sterile. In some embodiments, the protective cover is not required to be sterile. The term "sterile" refers to a degree of cleanliness that meets medical guidelines set by the appropriate agency, e.g., the U.S. FDA for U.S. devices and similar regulatory guidelines outside the U.S.) for surgical use.

Figure 3A:
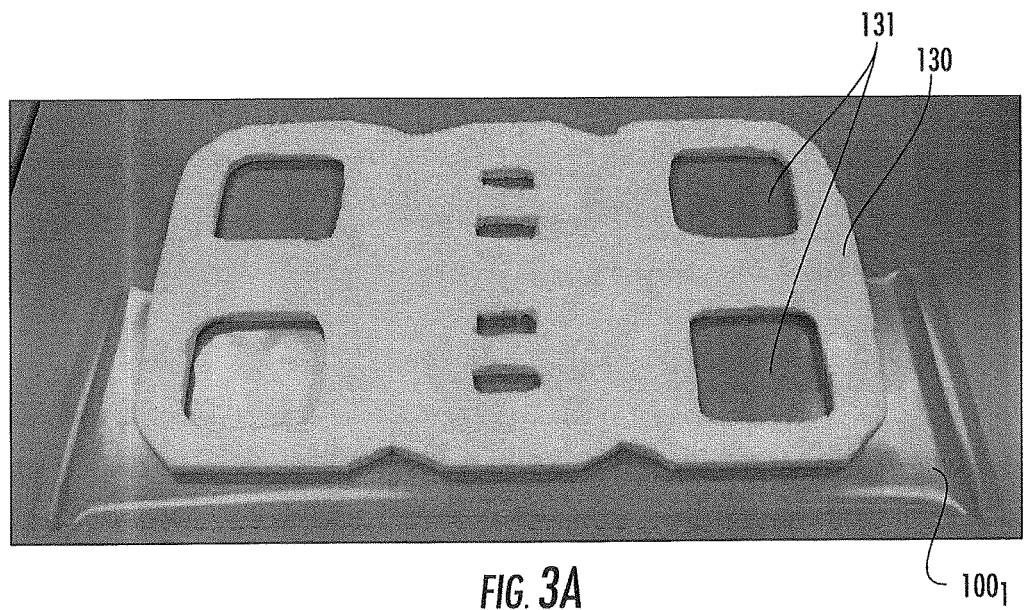
FIGS. 3A and 3B are front perspective views of a flex coil on top of the first layer or first sheet of a protective cover with the adhesive, sticky and/or tacky side facing up, according to embodiments of the present invention.
Figure 3B:
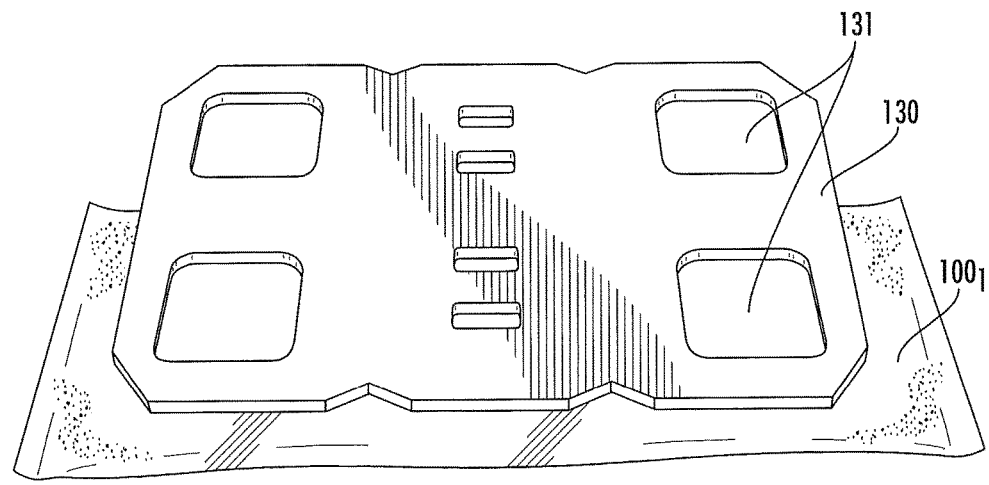
Figure 4A:
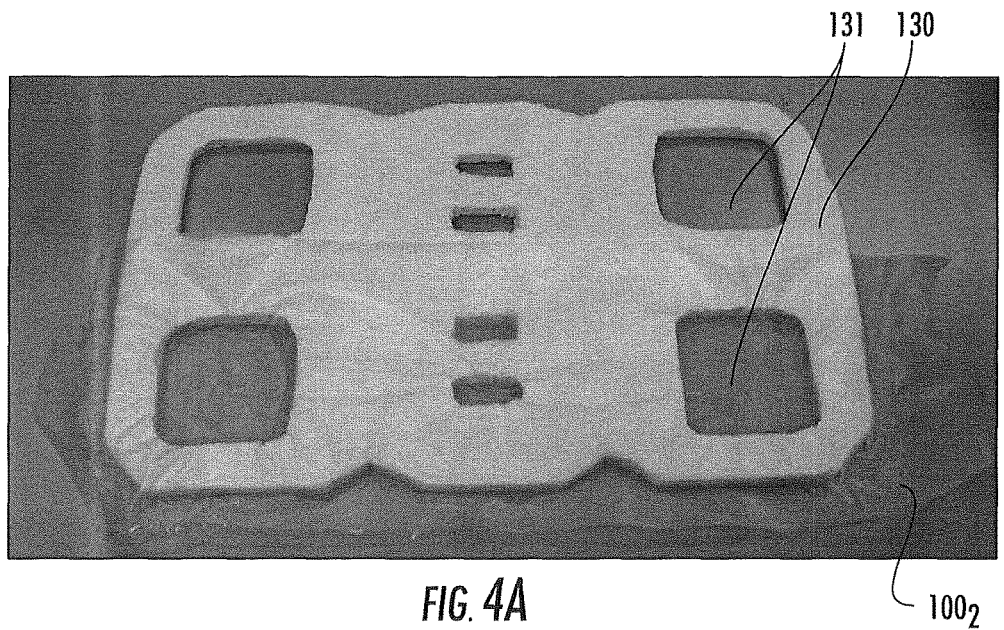
FIGS. 4A and 4B is a front perspective view of the flex coil shown in FIGS. 3A and 3B, with a second sheet of the protective cover laid on top of the flex coil, adhesive, sticky or tacky side down, according to embodiments of the present invention.
Figure 4B:
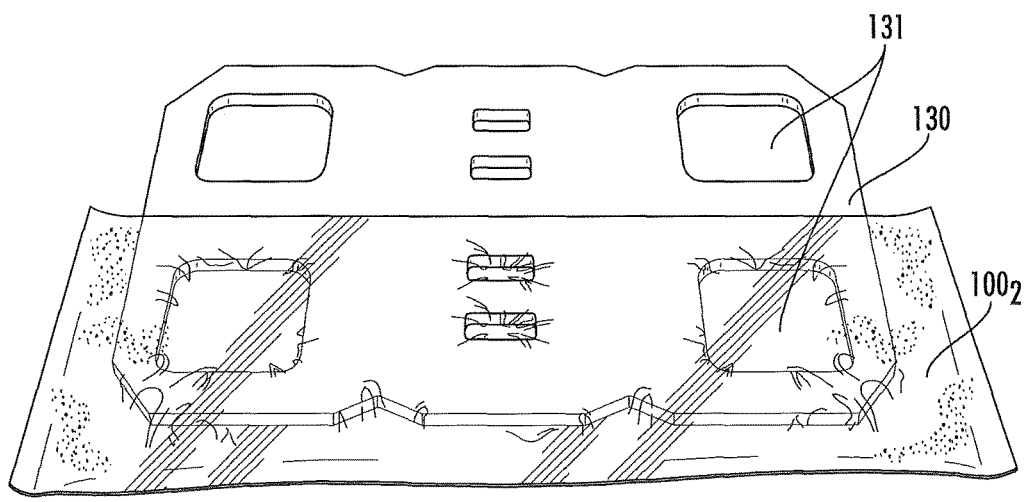
Figure 5A:
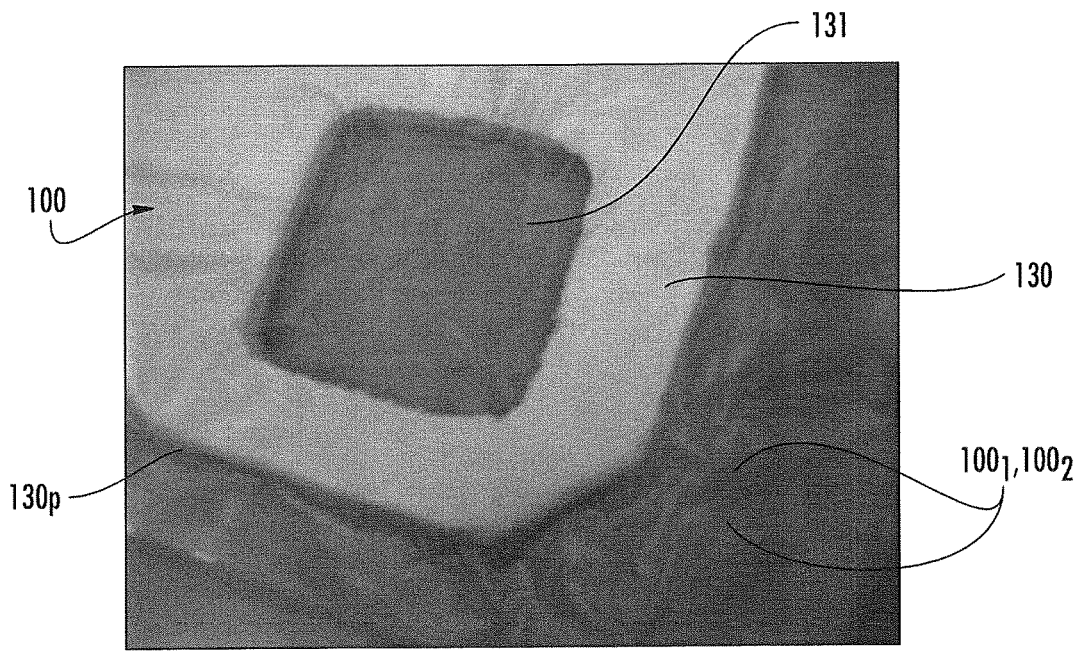
FIGS. 5A and 5B are enlarged, partial front perspective views of the flex coil and protective cover shown in FIGS. 4A and 4B, illustrating respective inner primary surfaces of the two sheets of the protective cover pressed together particularly around the perimeter of the coil and/or perimeter of shaped openings to completely seal the coil therein according to embodiments of the present invention.
Figure 5B:
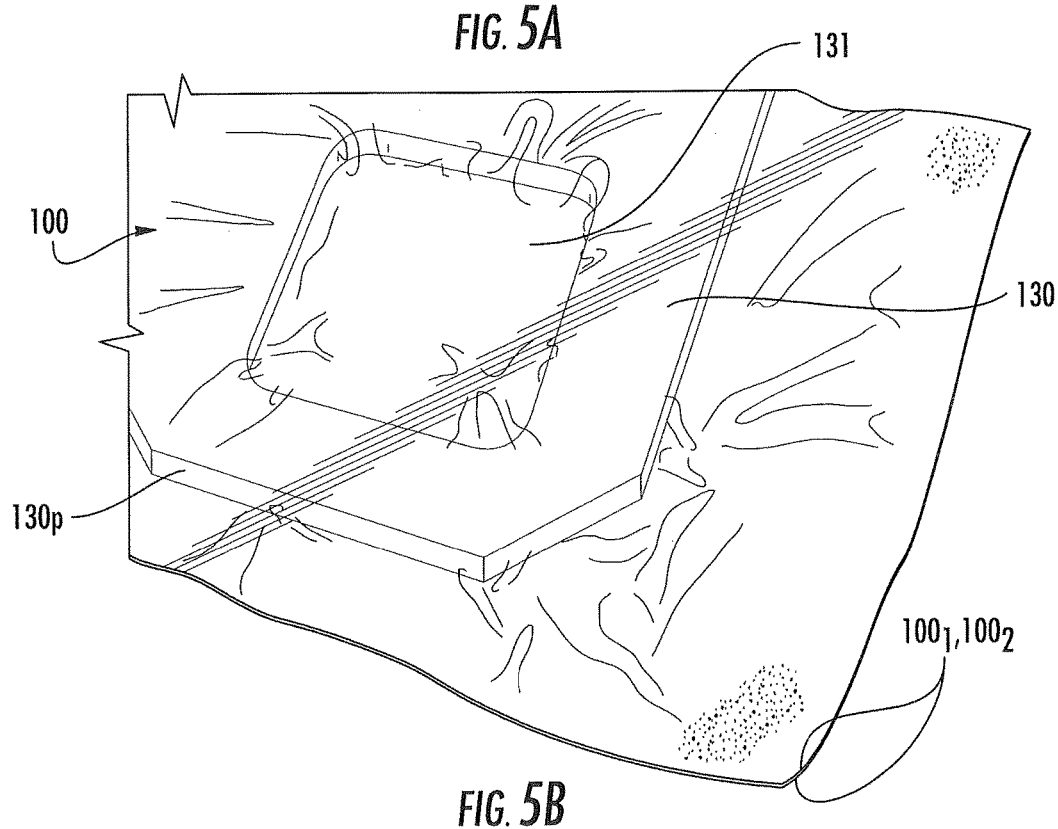
Figure 6A:
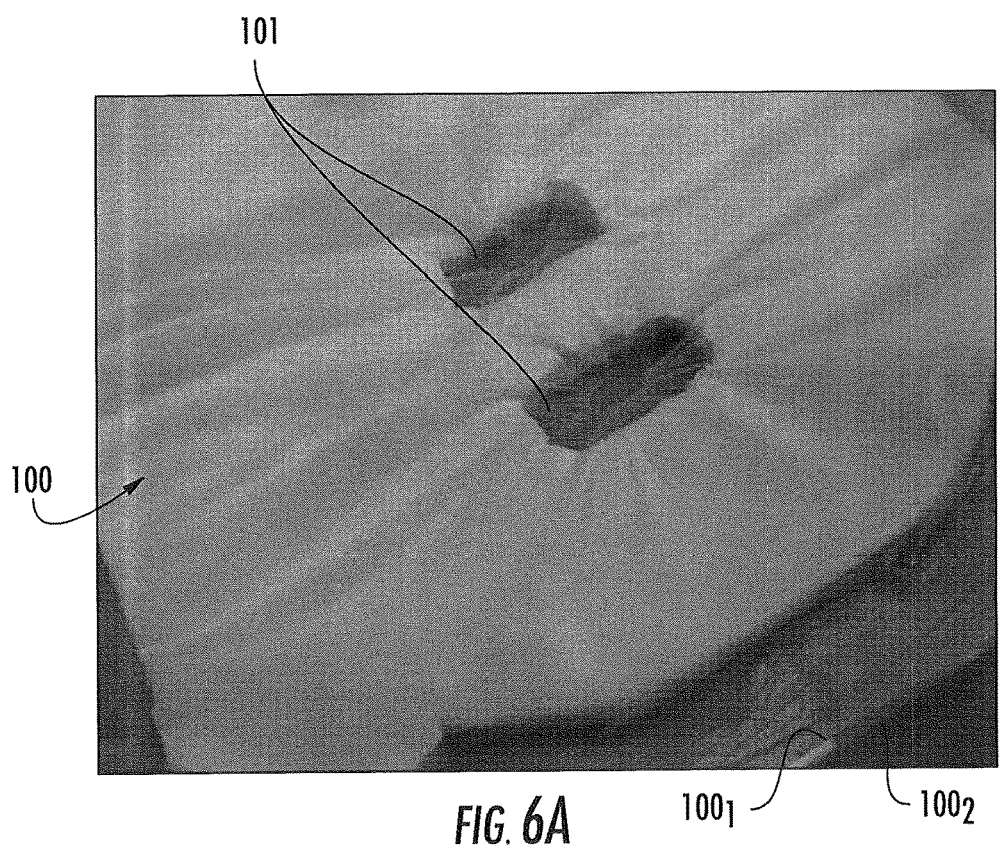
FIGS. 6A, 6B and 7A, 7B are views of different portions of the RF coil sealed in the protective cover shown in FIGS. 2A, 2B-4A, 4B according to embodiments of the present invention.
Figure 6B:
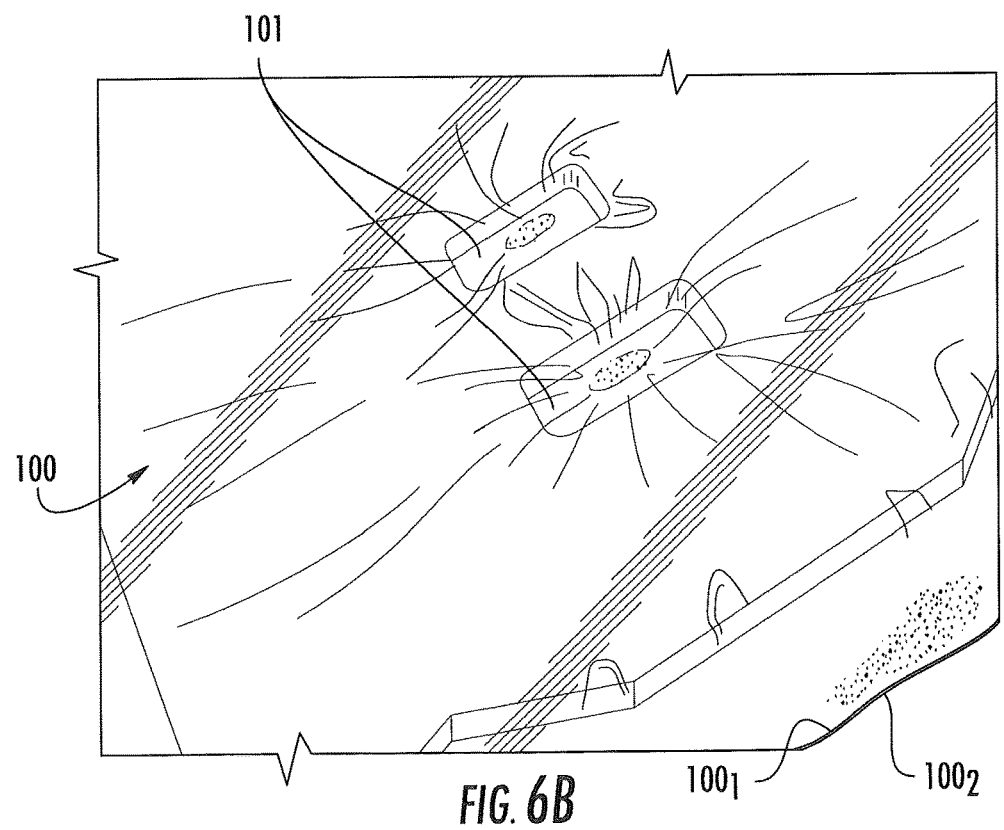
Figure 7A:
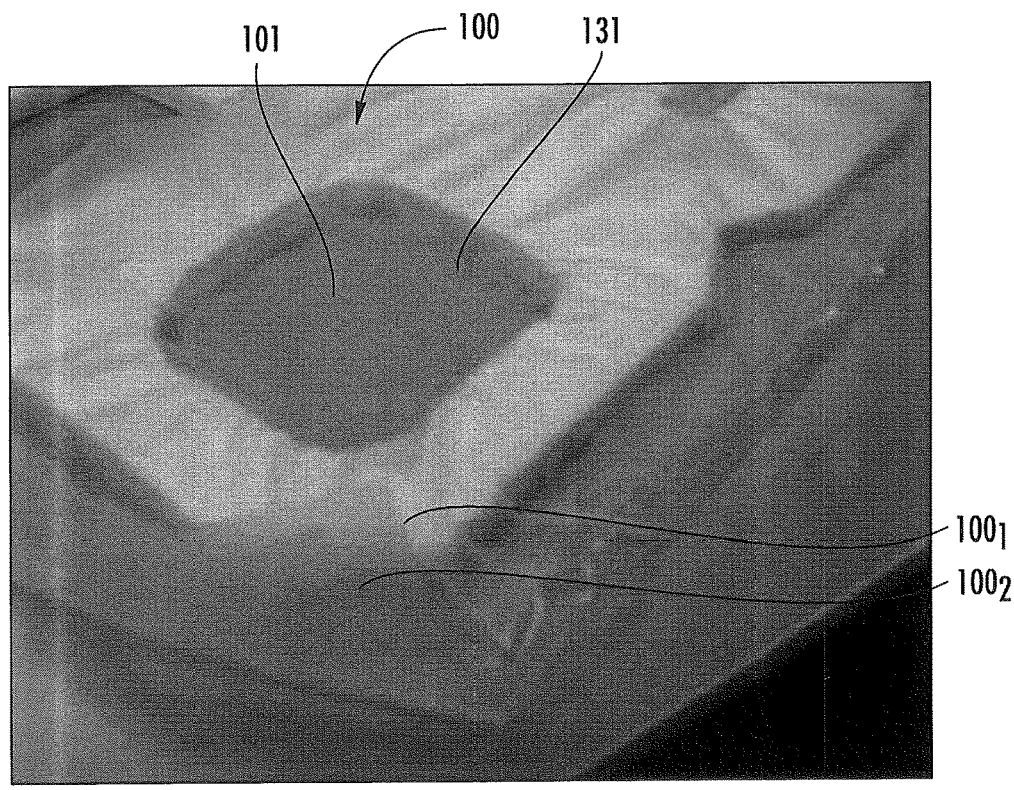
Figure 7B:
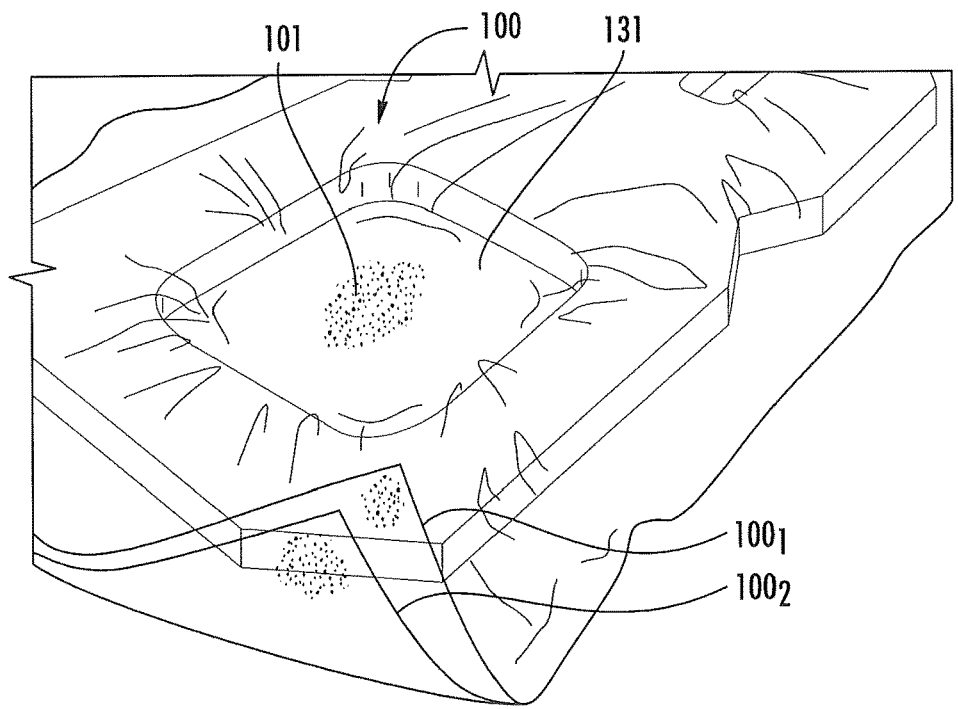

Turning now to the figures, flexible imaging coils 130 (FIGS. 1, 3A, 3B) have protective covers 100. The flexible imaging coils 130 can be in various shapes like donuts or waffles and are typically about 0.5 inches to about 1 inch thick with a tactile feel similar to foam rubber. The coils 130 are typically malleable. The head fixation pins 150 (FIG. 1) go through holes or windows 131 (FIG. 3A, 3B) in the coil 130. The coil(s) 130 can be positioned around the patients head (FIG. 1).

It is noted that FIGS. 2A, 3A, 4A, 5A, and 6A are digital photographs of a prototype cover and exemplary flex coil configuration. FIGS. 2B, 3B, 4B, 5B and 6B are respective counterpart line drawings of the photographs to comply with various patent office rules.

To protect the coil 130 from blood and other fluids, a user (e.g., typically a clinician prior to surgery) can place a self-sticking, peelably removable protective cover 100 over the RF coil 130, typically when the RF coil is in a flat configuration. The flex coil with the cover can then be shaped into a desired non-flat geometry for surgical use/placement.

The cover 100 can be provided as a continuous roll that a user can cut to size for particular RF coils at use sites. The cover 100 can be provided as one or a plurality of pre-cut sheets from a supplier to allow appropriate sizes without requiring sizing at a use site. Different RF coils may have different pre-cut sizes. The cover 100 can also or alternatively be provided in a continuous or roll with or without preferential scoring (e.g., pre-cut marks that do not break through an entire thickness, e.g., not through perforations so as to maintain the seal capability) similar to a roll of paper towels or food covering material.

Referring to FIGS. 3A, 3B-7A, 7B, in some embodiments, the cover 100 can include at least one upper sheet $100_1$, and at least one lower sheet $100_2$, which reside on respective upper and lower external surfaces of the coils 130.

The sheets $100_1$, $100_2$ can be pressed together to encapsulate and seal the coil 130 therein, e.g., a manual "press to seal" operation by a user and the cover 100 can be easily peeled away from the RF coil after use to form a single-use disposable protective cover.

The sheet or sheets 100, $100_1$, $100_2$ can be held in a package and the package can have a label that identifies it for medical use and/or for flexible RF coils associated with MRI environments. The sheet or sheets 100, $100_1$, $100_2$ can be sold or offered for sale under a product number by a medical parts supplier.

A clinician/user can introduce holes, e.g., puncture, cut or pierce 101, where needed, for the head fixation frame pins 150. The pins 150 can be used to form the holes 101 during attachment of the pins 150 to the patient or other puncture or hole introduction tools can be used prior to or after attachment of the cover 100 to the respective head coil 130.

In some embodiments, apertures or holes can be pre-formed or partially preformed in one or more sheets 100 and/or the one or more sheets can be scored to have a section preferentially configured or marked for facilitating puncture or incision or other formation of the access path/hole in mating components of the cover, e.g., opposing surfaces of sheets $100_1$, $100_2$. In some embodiments, the sheets can have visual indicia to indicate a desired fixation pin location that extends over an open space of a respective flexible RF coil.

In some embodiments, the holes 101 can be pre-formed in respective sheets $100_1$, $100_2$ and packaged and sold ready-to-use so that a user/clinician can simply press/place on a desired RF coil 130.

The protective cover 100 can be easily, peelably removed after a respective surgery.

Figure 8:
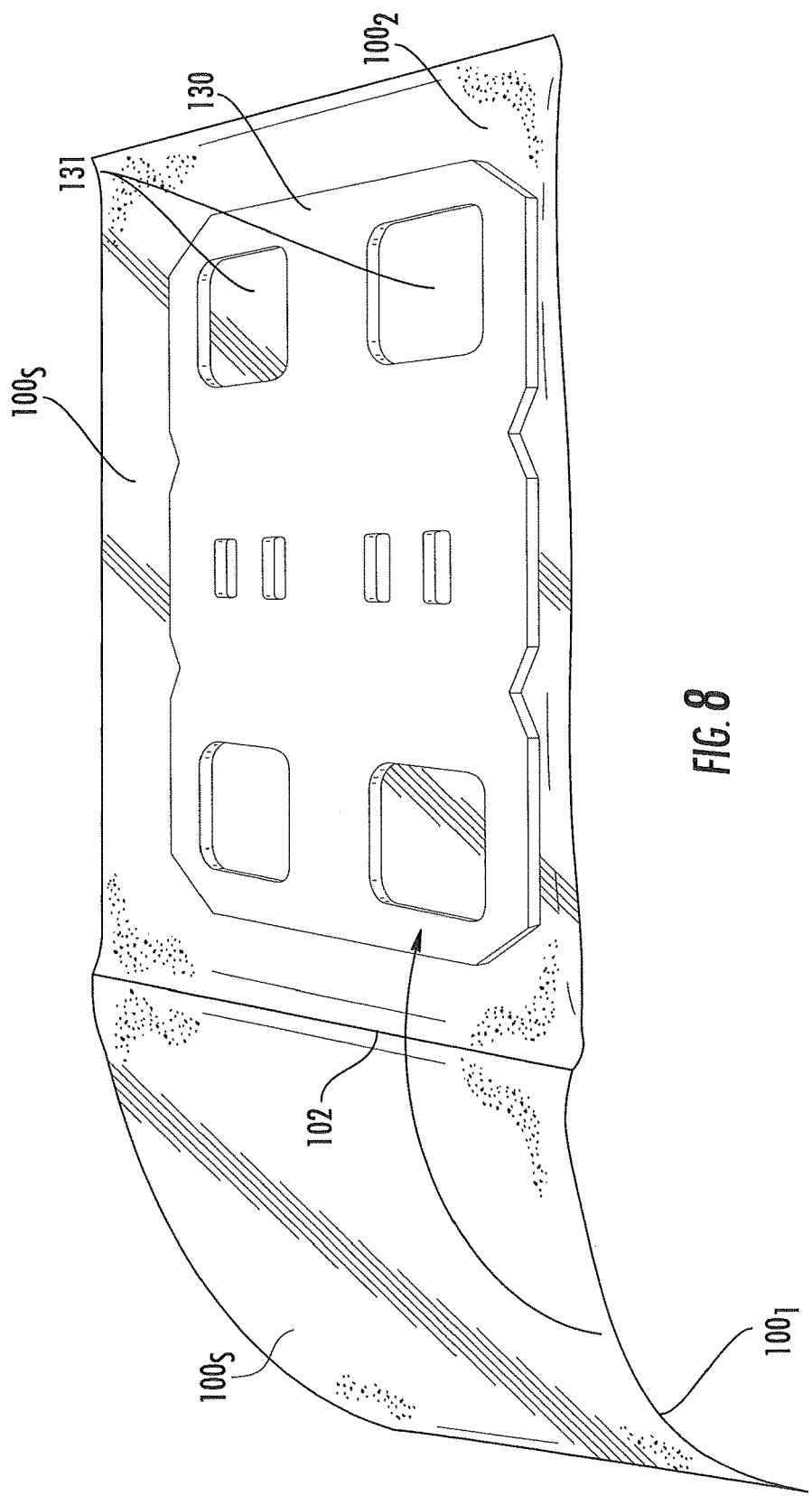
FIG. 8 is a schematic front perspective view of a protective cover that can be sized and configured to have at least one fold segment/line according to embodiments of the present invention.

Although shown as using four sheets, two top sheets $100_1$ and two bottom sheets $100_2$ that cooperate to form a respective cover 100, less or more sheets may be used. For example, as shown in FIG. 8, a single sheet can form the protective cover 100 by folding along one fold line 102 to form one outer edge of the cover along the fold line.

The sheet/sheets of the cover may extend a distance outside the outermost perimeter of the coil(s) a distance of between about 1-3 inches, typically about 2 inches. FIG. 1 illustrates an exemplary head fixation assembly 10. As shown, the assembly 10 includes a base 20 and a head support frame 60 movably secured to the base 20. The base 20 and head support frame 60 are MRI compatible. The base 20 can be designed to accept different types of head support frames 60 and/or mount to different gantries from various manufacturers. Embodiments of the present invention are not limited to the head fixation assembly shown.

The illustrated base 20 includes spaced apart first and second supports 22a, 22b connected by an elongated member 24 secured therebetween. In some embodiments, the first and second supports 22a, 22b are configured to be secured to a gantry "G" associated with an MRI scanner. However, a variety of ways of securing the base 20 to a gantry G may be utilized.

In some embodiments of the present invention, the base 20 may not be attached directly to an MRI scanner gantry. Instead, the base 20 may be configured to be connected to or integrated with another device that could be received and secured to an MRI scanner or to a gantry associated with an MRI scanner. As such, embodiments of the present invention are not limited to the illustrated configuration of base 20 and supports 22a, 22b. The MRI compatible base 20 can be configured to receive a head support frame 60 and allow the head support frame to be moved along the base 20 relative to a gantry of an MRI scanner can have various configurations. Further details of this embodiment of the head fixation assembly are described in co-pending U.S. patent application Ser. No. 13/781,117, the contents of which are hereby incorporated by reference as if recited in full herein.

All of the components of the head fixation assembly 10 described above (i.e., the base 20, the head support frame 60, etc.) are formed from or include MRI-compatible material. Exemplary MRI-compatible (non-ferromagnetic) materials include, but are not limited to, various polymeric materials (e.g., plastics), carbon fiber materials, glass-filled epoxies, and metals such as nickel-titanium alloys (e.g., Nitinol) or suitably SST. As known to those skilled in the art of MRI, Nitinol is non-ferromagnetic with a lower magnetic susceptibility than conventional stainless steel.

Some embodiments are directed to methods of preparing a flexible RF coil of an MR scanner for a medical procedure. The methods include providing at least one sheet of self-sticking film, placing the film about the flexible RE coil while the RF coil is in a flat or substantially flat orientation, then pressing the film together to encase the RF coil; and orienting the RF coil so that sides extend upwardly. The methods can include extending fixation pins through the film and through gap spaces of the RF coil. The methods can include peelably removing the film after a medical procedure.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A package for a medical procedure, the package comprising a film that is a press-to-seal, self-sticking and peelably removable film sized and configured to directly and releasably encase a flexible RF coil associated with MRI scanners, wherein the film has a first primary surface and a second primary surface that opposes the first primary surface, the first primary surface being non-sticky and/or non-tacky and the second primary surface being sticky and/or tacky, and wherein the film is a single use disposable film.

2. The package of claim 1, wherein the package is labeled for MRI RF coils, wherein the press-to-seal self-sticking and peelably removable film is a single layer film, and wherein the press-to-seal, self-sticking and peelably removable film is adhesive-less and sticks to itself but not a respective flexible RF coil while encasing the respective RF coil such that, after peelably removed from a respective flexible RF coil, the film leaves no adhesive residue on the flexible RF coil.

3. The package of claim 1, wherein the press-to-seal, self-sticking and peelably removable film has indicia and/or scored segments that do not extend through an entire thickness for identifying aperture locations for fixation pins that extend through open spaces in a respective flexible RF coil.

4. The package of claim 1, wherein the press-to-seal, self-sticking and peelably removable film is a single layer of film or two single layers of film and has pre-formed apertures for fixation pins that, in use, extend through open spaces in respective RF coils.

5. The package of claim 1, further comprising a plurality of head fixation pins and a head fixation frame, wherein the press-to-seal, self-sticking and peelably removable film extends over open window spaces residing between adjacent members of a malleable RF coil body of the flexible RF coil that allow the head fixation pins to extend therethrough, and wherein the film extends over opposing sides of the open window spaces and directly attaches to facing surfaces of the film at the open window spaces.

6. The package of claim 1, wherein the film is a sheet or sheets of a single layer and visually transmissive film of adhesive-less co-extruded polyethylene.

7. A flexible RF coil for MRI systems, the flexible RF coil having a body with a malleable shape and comprising a plurality of externally open through spaces extending through external spaced apart segments of the body, the flexible RF coil comprising an external conformable cover, wherein the external conformable cover is a peelably removable, self-sticking film that sealably totally encloses the flexible RF coil therein, and wherein first and second layers of the film extend across the plurality of the externally open through spaces and are directly attached to each other from opposing sides of at least some of the external open spaces.

8. The flexible RF coil of claim 7, wherein the flexible RF coil is a flexible RF head coil, wherein the body can have a flat orientation and a shaped orientation where opposing outer end portions extend upwardly to position an upper end thereof above a head of a patient, and wherein the external conformable cover of the peelably removable, self-sticking film is a single layer self-sticking film that extends outside an outermost perimeter of the RF coil a distance in a range of 1-3 inches.

9. The flexible RF coil of claim 7, further comprising at least one pin aperture extending through directly attached portions of the first and second layers of the film of the external conformable cover and a corresponding at least one of the plurality of externally open through spaces of the flexible RF coil.

10. The flexible RF coil of claim 7, wherein the external conformable cover comprises either (a) first and second overlying sheets of a single layer film as the first and second layers of film, with an outer surface being non-sticky and/or non-tacky and an inner surface being sticky and/or tacky or (b) first and second folded layers of a single sheet of a single layer film as the first and second layers, with an outer surface being non-sticky and/or non-tacky and an inner surface being sticky and/or tacky that extend over the plurality of externally open through spaces of the flexible RF coil and abut each other and releasably attach together to only stick to each other and are peelably removable without leaving any adhesive residue and/or tacky residue on the flexible RF coil.

11. The flexible RF coil of claim 10, wherein the first and second overlying sheets of the single layer of film or the folded layers of the single sheet of the single layer of film can be punctured with a fixation pin extending from a fixation assembly to a patient or subject through the first and second overlying sheets or the folded layers of the single sheet and one of the plurality of externally open through spaces of the body while the external conformable cover remains on the flexible RF coil without tearing.

12. The flexible RF coil of claim 7, used in combination with a head fixation assembly with a base formed entirely of MRI compatible material.

13. The flexible RF coil of claim 12, wherein the base is configured to be secured to a gantry associated with an MRI scanner and to extend across a width of the gantry.

14. The flexible RF coil of claim 13, wherein the flexible RF coil is a flexible RF head coil sized and configured to extend about a patient's head during an MRI imaging and/or interventional session, wherein the base is configured to removably receive an MRI compatible head support frame for adjustably immobilizing the head of a patient during a medical procedure, and to allow the MRI compatible head support frame to be moved to any of a plurality of locations across the width of the gantry, wherein the base is configured to allow the MRI compatible head support frame to rotate about two orthogonal axes so as to be positioned at any of a plurality of angles relative to the gantry, and can allow the MRI compatible head support frame to slide along the base to any of a plurality of positions relative to the width of the gantry.

15. The flexible RF coil of claim 13, wherein the first and second layers of the peelably removable, self-sticking film conformably attach to opposing primary surfaces of the body of the flexible RF coil, extend across the plurality of externally open through spaces and extend outside perimeter edges of the body of the flexible RF coil a distance in a range of 1-3 inches in abutting contact to thereby peelably, releasably seal the body of the flexible RF coil therein.

16. The flexible RF coil of claim 7, wherein the peelably removable, self-sticking film is visually transmissive, wherein the flexible RF coil is a flexible RF head coil sized and configured to extend about a patient's head during an MRI imaging and/or interventional session, and wherein the body is a malleable body that can be shaped from a two-dimensional flat shape to a self-supporting three-dimensional shape for a configuration suitable to extend spaced apart from but adjacent the patient's head during the MRI imaging and/or interventional session.

17. The flexible RF coil of claim 7, wherein the first and second layers of the film of (a) conformably attach to opposing primary surfaces of the body of the flexible RF coil and (b) extend across the plurality of external open spaces and outside perimeter edges of the body of the flexible RF coil a distance in a range of 1-3 inches in abutting contact to thereby seal the body of the flexible RF coil therein.

18. The flexible RF coil of claim 7, wherein the film is a sheet or sheets of a single layer and visually transmissive film of adhesive-less co-extruded polyethylene.

\* \* \* \* \*